(12) United States Patent
Lee (10) Patent No.: US 9,044,476 B2
(45) Date of Patent: Jun. 2, 2015

(54) USE OF URARIA IN PROMOTING OSTEOGENESIS OR PROVIDING NEUROPROTECTION

(71) Applicant: Mei-Hsien Lee, Taipei (TW)

(72) Inventor: Mei-Hsien Lee, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 0 days.

(21) Appl. No.: 13/742,717

(22) Filed: Jan. 16, 2013

(65) Prior Publication Data

US 2014/0200194 A1 Jul. 17, 2014

(51) Int. Cl.
| | |
|---|---|
| *A61K 31/70* | (2006.01) |
| *A61K 36/48* | (2006.01) |
| *A61K 31/7048* | (2006.01) |
| *C07H 7/06* | (2006.01) |

(52) U.S. Cl.
CPC ............. *A61K 36/48* (2013.01); *A61K 31/7048* (2013.01); *C07H 7/06* (2013.01); *A61K 2236/00* (2013.01)

(58) Field of Classification Search
CPC A61K 36/48; A61K 31/7048; A61K 2236/00
USPC ............................... 514/27, 53; 536/6, 123.13
See application file for complete search history.

(56) References Cited

U.S. PATENT DOCUMENTS

| | | | |
|---|---|---|---|
| 5,478,549 A | 12/1995 | Koch | |
| 6,340,703 B1 | 1/2002 | Kelly | |
| 7,122,214 B2 | 10/2006 | Xie | |
| 7,350,914 B2 | 4/2008 | Tanaami et al. | |
| 8,153,167 B2 | 4/2012 | Hwang et al. | |

OTHER PUBLICATIONS

Liu et al., Antihyperglycemic and antihyperlipidemic effect of Uraria crinita water extract in diabetic mice induced by STZ and food, Journal of Medicinal Plants Research, vol. 4(5), pp. 370-374, Mar. 4, 2010.*
Hamid et al., Anti-inflammatory and Analdesic Activity of Uraria lagopoides, Pharmaceutical Biology, 2004, vol. 42, No. 2, pp. 114-116.*
Xinxiang Wang et al., "Puerariae radix prevents bone loss in castrated male mice", Metabolism, 2005, 54: 1536-1541.
Ji-Cheon Jeong et al., "Stimulative effects of Drynariae Rhizoma extracts on the proliferation and differentiation of osteoblastic MC3T3-E1 cells", Journal of Ethnopharmacology, 2005, 96: 489-495.
Tsai-Pei Hsieh et al., "Icariin isolated from Epimedium pubescens regulates osteoblasts anabolism through BMP-2, SMAD4, and Cbfa1 expression", 2010, Phytomedicine, 17:414-423.
Koichi Machida et al., "Two new neolignan glycosides from leaves of Osmanthus heterophyllus", Journal of Natural Medicines, 2009, 63: 227-231.

* cited by examiner

*Primary Examiner* — Elli Peselev
(74) *Attorney, Agent, or Firm* — WPAT, P.C.; Anthony King; Kay Yang (57) ABSTRACT

The invention provides a method for promoting osteogenesis, increasing bone mass or enhancing the rate of bone growth, which comprises administering to a subject an effective amount of *Uraria*, a part thereof or an extract thereof. Also provided are a method for treating and/or preventing osteoporosis and a method for providing neuroprotection, comprising administering to a subject an effective amount of *Uraria*, a part thereof or an extract thereof.

10 Claims, 7 Drawing Sheets

USE OF URARIA IN PROMOTING OSTEOGENESIS OR PROVIDING NEUROPROTECTION

FIELD OF THE INVENTION

The invention relates to a method for prompting osteogenesis or providing neuroprotection with an herbal product. Particularly, the invention uses *Uraria* to promote osteogenesis or provide neuroprotection.

BACKGROUND OF THE INVENTION

Bone is the structural material of the body's framework and serves to maintain the necessary bone mass and structure. Bone contains calcium ($Ca^{2+}$) and plays an important role in maintaining the calcium level in the blood. To this end, the growth of bone is a metabolic balance between the activity of osteoblasts and osteoclasts in the bone remodeling cycle. When the balance between bone absorption and bone formation is disrupted, the amount of bone tissue replaced by osteoblasts fails to match that absorbed by osteoclasts, thus leading to osteoporosis, a common condition causing loss of bone density or bone mass. Osteoblasts are bone forming cells that originate from mesenchymal stem cells (MSCs). Osteoblasts have a very important role in creating and maintaining skeletal architecture. The formation of bone involves a complex series of events that include the proliferation and differentiation of osteoblasts, finally resulting in the mineralization of extracellular matrix. Specific genes are sequentially expressed or repressed during each stage of osteoblast development; for example, histone 4 is a marker for proliferation, alkaline phosphatase (ALP) for differentiation, and osteocalcin for mineralization. In terms of human health, bone formation is a key clinical concern for proper growth of bones in infants and children, prevention of bone mass loss in climacteric women, as well as healing and remodeling of bone fractures in patients. In order to prevent bone loss and increase bone formation, nutritional and pharmacological agents are needed. Therefore, in vitro models of osteoblast primary cell culture have been widely used to find new agents that induce osteoblast differentiation, matrix mineralization, and new bone formation. There are a number of parameters that influence the expression of the osteoblastic phenotype in cell culture.

Bone disease such as osteoporosis is common among middle-aged or elderly women. Examples of therapeutic agents used for osteoporosis include, but is not limited to, bisphosphonate products (alendronate, etidronate), hormone products (raloxifene), vitamin D products, calcitonin products and calcium products. However, bisphosphonate products have problems of low absorption rate and troublesome administration methods and may induce esophagitis. Hormone products require life-time administration and have potential side effects such as breast cancer, uterine cancer, cholelithiasis and thrombosis. Vitamin D products are expensive and not very effective. Calcitonin products also have problems of high cost and difficult administration. Calcium products have less side effects but are limited to prevention rather than treatment. Therefore, there is a need for new osteoporosis therapies.

Herbal therapies have increasingly been considered viable alternative treatments for various diseases. U.S. Pat. No. 5,478,549 relates to a method for orally inducing and enhancing the absorption of calcium into mammalian bone tissue comprising the administration of an effective dose of a flavonol aglycone glycoside in combination with nutritional calcium. U.S. Pat. No. 6,340,703 provides a method for the treatment or prevention of osteoporosis comprising administering to a subject in need of such treatment a therapeutically effective amount of the isoflavono formononetin optionally administered with one or more pharmaceutically acceptable adjuvants, carriers and/or excipients. U.S. Pat. No. 7,122,214 uses *Rhizoma Drynariae* extract (RDE) as therapeutic agent for osteoporosis. U.S. Pat. No. 7,350,914 provides a pharmaceutical or medicinal preparation comprising a mixture of herbs including *Glycine max*, *Coleus forskohlii*, *Camellia sinensis*, *Allium sativum*, *Withania somnifera*, *Boerhavia diffusa*, and *Curcuma longa*, or a mixture of the active ingredients that have been extracted from those herbs. U.S. Pat. No. 8,153,167 provides a composition derived from six plant materials: (i) *Herba epimedii* (Yin Yang Huo) (ii) *Fructus Psoraleae* (*Psoralea coryfolia*) (Bu Gu Zhi) (iii) Radix *Rehmanniae preparatae* (*Rehmannia glutinosa*) (Shu Di) (iv) *Cortex Eucommiae* (Du Zhong) (v) *Fructus Cnidii* (She Chuang Zhi) (vi) *Radix Astragali* (*Astragalus Membranaceus*) (Huang Qi); the composition is useful in treating conditions linked to the activity of osteoblasts and/or osteoclasts, such as osteoporosis and other conditions relating to bone mass or menopause, obesity, glucose intolerance, and diabetes. Other traditional Chinese herbal medicines having potential efficacy on bone formation in previous studies include *Puerariae radix* (Wang, X., Wu, J., Chiba, H., Yamada, K., & Ishimi, Y. (2005). *Puerariae radix* prevents bone loss in castrated male mice. Metabolism, 54, 1536-1541.), *Drynariae rhizome* (Jeong, J. C., Lee, J. W., Yoon, C. H., Lee, Y. C., Chung, K. H., Kim, M. G., & Kim, C. H. (2005). Stimulative effects of *Drynariae Rhizoma* extracts on the proliferation and differentiation of osteoblastic MC3T3-E1 cells. Journal of Ethnopharmacology, 96, 489-495.), and *Epimedium pubescens* (Hsieh, T. P., Sheu, S. Y., Sun, J. S., Chen, M. H., & Liu, M. H. (2010). Icariin isolated from *Epimedium pubescens* regulates osteoblasts anabolism through BMP-2, SMAD4, and Cbfa1 expression. Phytomedicine, 17, 414-423).

*Uraria crinita* (L.) Desv. Ex DC. (Fabaceae) is a traditional edible herb widely distributed throughout India, Thailand, Indonesia, southern China, and Taiwan. It is reported to be effective in repressing stress ulcers. *U. crinita* shows nitric oxide-scavenging and antioxidant effects in vitro (Luo, C., Liu, A. M., Xing, W. Q., Shi, G., Cao, Y., Pang, J. X., & Qiu, Y. C. (2011). Antioxidant effect of flavonoids from *Uraria crinita*. Zhongguo Shiyan Fangjixue Zazhi, 17, 198-201.). Its use for the treatment of coldness, swelling, stomachalgia, and ulcers may be due to its anti-inflammatory activities. In Taiwan, people cook it in water and drink it like ginseng tea for its flavor, fragrance, sweetness, and to quench thirst, and so it has been also called "Taiwanese ginseng." In addition, its roots have been used in Traditional Chinese medicine dietary supplementation for treatment of skeletal dysplasia in children, as well as sport-related, bone twist, sprain and strain injuries (Machida, K., Sakamoto, S., & Kikuchi, M. (2009). Two new neolignan glycosides from leaves of *Osmanthus heterophyllus*. Journal of Natural Medicines, 63, 227-231).

However, there are no reports showing that *U. crinita* is associated with bone diseases.

SUMMARY OF THE INVENTION

The invention provides a method for promoting osteogenesis, increasing bone mass or enhancing rate of bone growth, which comprises administering to a subject an effective amount of *Uraria* or a part thereof or an extract thereof.

The invention also provides a method for treating and/or preventing a bone disease, which comprises administering to a subject an effective amount of *Uraria*, a part thereof or an extract thereof.

The invention further provides a method for providing neuroprotection, which comprises administering to a subject an effective amount of *Uraria*, a part thereof or an extract thereof.

DETAILED DESCRIPTION OF THE INVENTION

The invention surprisingly found that *Uraria* or an extract thereof increases osteogenesis and is a stimulator for bone growth and repair and provides effect in neuroprotection.

DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The terms "a" and "an" refer to one or to more than one (i.e., to at least one) of the grammatical object of the article.

As used herein, the term "or" in the claims refers to "and/or" unless explicitly indicated to refer to alternatives only or unless the alternatives are mutually exclusive.

The term "promote," "promotion," and "promoting" refer to an increase in an activity, response, condition, disease, or other biological parameter.

The term "subject" includes living organisms such as humans, monkeys, cows, sheep, horses, pigs, cattle, goats, dogs, cats, mice, rats, cultured cells, and transgenic species thereof. In a preferred embodiment, the subject is a human.

The term "administering" includes routes of administration which allow the *Uraria* of the invention to perform their intended function.

The term "treat" or "treatment" is meant to indicate a method of reducing the effects of a disease or condition. Treatment can also refer to a method of reducing the underlying cause of the disease or condition itself. The treatment can also be any reduction from native levels and can be but is not limited to the complete ablation of the disease, condition, or the symptoms of the disease or condition.

The term "prevent," "prevention" or "preventing" means inhibition or averting of symptoms associated with osteoporosis.

The term "effective amount" means an amount of *Uraria* effective to treat and/or prevent osteoporosis or provide neuroprotection.

The term "osteogenic" or "osteogenesis" refers to proliferation of bone cells and growth of bone tissue (i.e., synthesis and deposit of new bone matrix) from undifferentiated stem cells and cells of osteoblast lineage. Osteogenesis also refers to differentiation or transdifferentiation of progenitor or precursor cells into bone cells (i.e., osteoblasts). Progenitor or precursor cells can be pluripotent stem cells including, e.g., mesenchymal stem cells. Progenitor or precursor cells can be cells pre-committed to an osteoblast lineage (e.g., pre-osteoblast cells) or cells that are not pre-committed to an osteoblast lineage (e.g., pre-adipocytes or myoblasts).

The term "bone disorder" refers to a disease associated with loss of bony tissue such as osteoporosis.

Methods for Promoting Osteogenesis and Treating and/or Preventing Osteoporosis

In one aspect, the invention provides a method for promoting osteogenesis, which comprises administering to a subject an effective amount of *Uraria* or a part thereof or an extract thereof.

In another aspect, the invention provides a method of increasing bone mass, which comprises administering to a subject an effective amount of *Uraria*, a part thereof or an extract thereof.

In a further aspect, the invention provides a method of increasing or enhancing the rate of bone growth, which comprises administering to a subject an effective amount of *Uraria*, a part thereof or an extract thereof.

In another further aspect, the invention provides a method for treating and/or preventing a bone disease, which comprises administering to a subject an effective amount of *Uraria*, a part thereof or an extract thereof.

Induction of osteogenesis, in vitro or in vivo, can be detected using any method known in the art. For example, by detecting expression of osteoblast-specific proteins, detecting expression of bone-specific transcription factors, and detecting changes in bone density. Osteoblast-specific proteins include, for example, alkaline phosphatase (ALP), collagen type I, osteocalcin, and osteoponin (see, e.g., Olsen et al., Annu. Rev. Cell. Dev. Biol. 16:191 (2000)). In some embodiments, expression of alkaline phosphatase is detected as an indicator of osteogenesis. Bone specific transcription factors include, for example, Cbfa1/Runx2, gsc, D1x1, D1x5, Msx1, Cart1, Hoxa1, Hoxa2, Hoxa3, Hoxb1, rae28, Twist, AP-2, M1f, Pax1, Pax3, Pax9, TBX3, TBX4, TBX5, and Brachyury (see, e.g., Olsen et al, 2000, supra).

The methods of the present invention can be used in treating bone diseases. Bone diseases that can be treated according to the invention, by increasing bone mass or bone growth include, but are not limited to, osteoporosis, arthritis, osteoarthritis, periodontal disease, alveolar bone loss, osteotomy bone loss, childhood idiopathic bone loss, curvature of the spine, and loss of height. Destructive bone disorders that can be treated according to the invention include, but are not limited to, osteoporosis, osteoarthritis and osteolytic lesions such as those caused by neoplastic disease, radiotherapy, or chemotherapy.

Bone diseases can be caused by a condition characterized by low bone mass, bone deficit, or cartilage defect. The term "bone mass" refers to bone mass per unit volume. A condition characterized by low bone mass is a condition where the level of bone mass is below the age specific normal level as defined in "Assessment of Fracture Risk and Its Application to Screening for Postmenopausal Osteoporosis," Report of a World Health Organization Study Group, World Health Organization Technical Series 843 (1994). A bone deficit is an imbalance in the ratio of bone formation to bone resorption, such that, if unmodified, the subject will exhibit less bone than desirable, or the subject's bones will be less intact and coherent than desired. Bone deficit can also result from fracture, from surgical intervention or from dental or periodontal disease. Bone healing includes, but is not limited to, repair of bone deficits, such as those occurring in, e.g., closed, open and non-union fractures. A cartilage defect is a damaged cartilage, less cartilage than desired, or cartilage that is less intact and coherent than desired.

Included in conditions characterized by low bone mass are, but are not limited to, primary and secondary osteoporosis, periodontal disease, alveolar bone loss, osteotomy bone loss, and childhood idiopathic bone loss. Conditions characterized by low bone mass also include, but are not limited to, long term complications of osteoporosis such as curvature of the spine, loss of height and prosthetic surgery.

Osteoporosis or porous bone is a disease characterized by net loss of bone mass per unit volume. The consequence of this loss of bone mass and resulting bone fracture is the failure of the skeleton to provide adequate structural support for the body, low bone mass and structural deterioration of bone tissue, leading to bone fragility and an increased susceptibility to fractures of the hip, spine, and wrist. Bone loss occurs without symptoms. Osteoporosis includes "secondary osteoporosis," such as glucocorticoid-induced osteoporosis, hyperthyroidism-induced osteoporosis, immobilization-induced osteoporosis, heparin-induced osteoporosis or immunosuppressive-induced osteoporosis. In people with osteoporosis, the bones can become so weak that a sudden strain can cause a fracture or cause a vertebra to collapse. Most current osteoporosis treatments stop continued bone loss but do not enhance bone formation and thus bone quality remains poor but does not get worse.

In one embodiment, any of the above-mentioned methods of the invention comprise a further step of administrating an additional osteogenesis-promoting agent. Preferably, the additional agent is selected from bisphosphonates. Preferred bisphosphonates include, but are not limited to, tiludronic acid, alendronic acid, zoledronic acid, ibandronic acid, risedronic acid, etidronic acid, clodronic acid, and pamidronic acid and their pharmaceutically acceptable salts. One skilled in the art will know that these compounds are often referred to by their ion form, e.g., tiludronate, alendronate, zoledronate, ibandronate, risedronate, etidronate, clodronate and pamidronate. Especially preferred bisphosphonates include alendronate and risedronate.

Methods for Providing Neuroprotection

In another aspect, the invention provides a method for providing neuroprotection, which comprises administering to a subject an effective amount of *Uraria*, a part thereof or an extract thereof.

Neuroprotection refers to the mechanisms and strategies used to protect against brain/neuronal injury or degeneration in the nervous system following acute disorders (e.g. stroke or brain or nervous system injury/trauma, hypoxia, spinal cord injury or peripheral nerve injury) or as a result of chronic neurodegenerative diseases (e.g. Parkinson's disease, Alzheimer's disease, multiple sclerosis). The goal of neuroprotection is to limit neuronal dysfunction/death after nervous system injury and attempt to maintain the highest possible integrity of cellular interactions in the brain, resulting in an undisturbed neural function. By providing neuroprotection, *Uraria* or a part thereof or an extract thereof can be used to treat neuronal injury (such as stroke, particularly ischemic stroke, brain injury, hypoxia, spinal cord injury or peripheral nerve injury) and treat or prevent neurodegenerative diseases.

*Uraria* or a Part or an Extract Thereof Used in the Methods of the Invention

*Uraria* is a genus of flowering plants in the legume family, Fabaceae. It belongs to the sub family Faboideae. In one embodiment of the invention, the *Uraria* is selected from the group consisting of: *Uraria crinita* (L.) Desv. ex DC., *Uraria lagopodioides* (L.) Desv. ex DC., *Uraria picta* (Jacq.) Desv. ex DC., *Uraria neglecta* Prain, *Uraria acaulis* Schindl, *Uraria acuminata* Kurz, *Uraria balansae* Schindl., *Uraria barbata* Lace, *Uraria campanulata* (Benth.) Gagnep., *Uraria candida* Backer, *Uraria clarkei* Gagnep., *Uraria cochinchinensis* Schindl., *Uraria cordifolia* Wall., *Uraria crinita* (L.) DC., *Uraria cylindracea* Benth., *Uraria fujianensis* Y. C. Yang & P. H. Huang, *Uraria gossweileri* Baker f., *Uraria kurzii* Schindl., *Uraria lacei* Craib, *Uraria lagopodoides* (L.) DC., *Uraria lagopus* DC., *Uraria longibracteata* Y. C. Yang & P. H. Huang, *Uraria pierrei* Schindl., *Uraria poilanei* Phon, *Uraria prunellifolia* Baker, *Uraria rotundata* Craib, *Uraria rufescens* (DC.) Schindl. and *Uraria sinensis* (Hemsl.) Franch. More preferably, the *Uraria* is *Uraria crinita* (L.) Desv. ex DC., *Uraria lagopodioides* (L.) Desv. ex DC., *Uraria picta* (Jacq.) Desv. ex DC. or *Uraria neglecta* Prain. Most preferably, the *Uraria* is *Uraria crinita* (L.) Desv.

ex DC. Preferably, the *Uraria* extract is an extract of *Uraria crinita* (L.) Desv. ex DC., *Uraria lagopodioides* (L.) Desv. ex DC., *Uraria picta* (Jacq.) Desv. ex DC. or *Uraria neglecta* Prain. More preferably, the *Uraria* extract is *U. crinite* extract.

The whole *Uraria* plant or all the parts of the *Uraria* plant can be used in the invention. In one embodiment, the roots of *Uraria* are used in the invention.

In one embodiment, an extract of *Uraria* can be used in the invention. Preferably, *Uraria crinita* (L.) Desv. ex DC., *Uraria lagopodioides* (L.) Desv. ex DC., *Uraria picta* (Jacq.) Desv. ex DC. or *Uraria neglecta* Prain is used to obtain the extract. Most preferably, the *Uraria* is *Uraria crinita* (L.) Desv. ex DC. More preferably, *Uraria crinita* (L.) Desv. ex DC. is used to obtain the extract. Preferably, the extract is organic solvent extract of the whole *Uraria* plant; more preferably the extract is the organic solvent extract of *Uraria* roots. Preferably, the extract is methanol extract, ethanol extract, extract, propanol extract, butanol extract or hexane extract. More preferably, the extract is ethanol extract. According to an embodiment of the invention, the organic solvent extract can be further partitioned with a sequence of hexane, ethyl acetate and butanol to obtain hexane extract, ethyl acetate extract and butanol extract. Accordingly, the invention provides an *Uraria* extract, which is produced by the following steps: extracting *Uraria* with ethanol to obtain an ethanol extract and extracting the ethanol extract with ethyl acetate or butanol to obtain an ethyl acetate extract or butanol extract. The ethyl acetate extract can be further partitioned to obtain nine fractions. The third fraction of these fractions is further separated by Sephadex LH-20 column chromatography and eluted with methanol/water to obtain seventeen fractions. The resulting fractions can be further separated by chromatography. As a result, a new compound, Apigenin 6-C-(β-D-apiofuranosyl(1→2)-α-D-xylopyranoside, can be obtained. Accordingly, the invention provides an *Uraria* extract, which is obtained by extracting *Uraria* to obtain an ethanol extract and extracting the ethanol extract with ethyl acetate or butanol to obtain an ethyl acetate extract or butanol extract.

Any extraction technique known in this art may be employed to prepare the extract according to the invention. The resulting extract can be further fractioned by chromatography. Preferred chromatography is liquid phase chromatography using solvent elution. Preferably, the liquid chromatography is high performance liquid chromatography (HPLC) or reverse-phase HPLC.

New Compounds Isolated from *Uraria* or a Part or an Extract Thereof

The invention provides the following new compound which is isolated from the *Uraria* or a part or an extract thereof:

Apigenin 6-C-(β-D-apiofuranosyl(1→2)-α-L-arabinopyranoside

Accordingly, the invention provides a compound of formula (I), wherein $R_1$ is apiofuranosyl-α-L-arabinopyranosyl, apiofuranosyl-β-D-glucopyranosyl, apiofuranosyl-β-D-galactopyranosyl, apiofuranosyl-β-D-xylopyranosyl, apiofuranosyl-β-D-arabinopyranosyl, apiofuranosyl-β-D-ribopyranosyl, apiofuranosyl-β-D-lyxopyranosyl, apiofuranosyl-β-D-ribulopyranosyl, apiofuranosyl-β-D-xylulose, apiofuranosyl-O-D-allo pyranosyl, apiofuranosyl-β-D-altropyranosyl, apiofuranosyl-β-D-mannopyranosyl, apiofuranosyl-β-D-gulopyranosyl, apiofuranosyl-β-D-idopyranosyl, apiofuranosyl-β-D-talosyl, apiofuranosyl-α-L-glucopyranosyl, apiofuranosyl-α-L-galactopyranosyl, apiofuranosyl-α-L-xylopyranosyl, apiofuranosyl-α-L-arabinopyranosyl, apiofuranosyl-α-L-ribopyranosyl, apiofuranosyl-α-L-lyxopyranosyl, apiofuranosyl-α-L-ribulopyranosyl, apiofuranosyl-α-L-xylulose, apiofuranosyl-α-L-allo pyranosyl, apiofuranosyl-α-L-altropyranosyl, apiofuranosyl-α-L-mannopyranosyl, apiofuranosyl-α-L-gulopyranosyl, apiofuranosyl-α-L-idopyranosyl or apiofuranosyl-α-L-talosyl.

Preferably, $R_1$ is apiofuranosyl-α-L-arabinopyranosyl, apiofuranosyl-β-D-arabinopyranosyl, apiofuranosyl-β-D-glucopyranosyl, apiofuranosyl-β-D-galactopyranosyl, apiofuranosyl-β-D-xylopyranosyl or apiofuranosyl-β-D-arabinopyranosyl. More preferably, $R_1$ is apiofuranosyl-α-L-arabinopyranosyl.

The compounds of formula (I) with different glycosyl group in $R_1$ can be modified from apigenin 6-C-(β-D-apiofuranosyl(1→2)-α-L-arabinopyranoside according to methods known in the art (see Org. Biomol. Chem., 2010, 8, 4451-4462). The synthesis scheme of linking various glycosyl group in $R_1$ to apigenin (4',5,7-trihydroxyflavone) is shown as follows:

-continued

Reagents and conditions: (a) BnBr, K$_2$CO$_3$ (1 equiv.), DMF, 25° C.; (b) Ac$_2$O, pyridine, DMAP; (c) NaBH$_4$, THF—H$_2$O, 0° C.; (d) cat. TMSOTf, CH2Cl2, -15 to 25° C.; (3 h); (e) AcCl, Et$_3$N, DMAP, CH$_2$Cl$_2$, RT;
(f) CAN, MeCN•AcOH—H$_2$O, 50° C.; (g) cat. I$_2$, DMSO; (h) H$_2$, Pd/C;
(i) Ac$_2$O, pyridine; (j) MeONa, MeOH.

Formulations and Methods of Administration

The *Uraria*, a part thereof or an extract thereof can be formulated with a pharmaceutically acceptable carrier, excipient, diluent and/or salt as a pharmaceutical composition or medicament for administration.

A pharmaceutically acceptable carrier, diluent, excipient, and/or salt means that the carrier, diluent, excipient and/or salt must be compatible with the other ingredients of the formulation, does not adversely affect the therapeutic benefit of the *Uraria*, a part thereof or an extract thereof, and is not deleterious to the recipient thereof.

Administration of the *Uraria*, a part thereof or an extract thereof or pharmaceutical compositions thereof for practicing the present invention can be by any method that delivers the compounds systemically and/or locally (e.g., at the site of the bone fracture, osteotomy, or orthopedic surgery). These methods include oral routes, parenteral routes, intraduodenal routes, etc.

In local applications, the *Uraria*, a part thereof or an extract thereof or pharmaceutical composition is applied to the sites of bone fractures, osteotomies or grafts, for example, either by injection of the *Uraria*, a part thereof or an extract thereof in a suitable solvent (e.g., an oily solvent such as arachis oil) to the fracture site or bone healing site or, in cases of open surgery, by local application thereto of such *Uraria*, a part thereof or an extract thereof in a suitable carrier such as bone-wax, demineralized bone powder, polymeric bone cements, bone sealants, polylactic acid, polyglycolic acid, polylactic acid-polyglycolic acid, etc. Alternatively, local application can be achieved by applying a solution or dispersion of the *Uraria*, a part thereof or an extract thereof in a suitable carrier onto the surface or incorporating it into solid or semi-solid implants conventionally used in orthopedic surgery, such as dacron-mesh, gel-foam and kiel bone, or prostheses.

For topical applications, the *Uraria*, a part thereof, an extract thereof or pharmaceutical composition thereof can be formulated in a suitable ointment containing the active component suspended or dissolved in one or more carriers. Carriers for topical administration of the *Uraria*, a part thereof or an extract thereof of this invention include, but are not limited to, mineral oil, liquid petrolatum, white petrolatum, propylene glycol, polyoxyethylene, polyoxypropylene compound, emulsifying wax, sugars such as lactose and water. Alternatively, the pharmaceutical compositions can be formulated in a suitable lotion or cream containing the *Uraria*, a part thereof or an extract thereof suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Depending on the particular condition, disorder or disease to be treated, additional therapeutic agents can be administered together with the *Uraria*, a part thereof or an extract thereof. Those additional agents can be administered sequentially in any order, as part of a multiple dosage regimen, from the *Uraria*- or its part- or its extract-containing composition (consecutive or intermittent administration). Alternatively, those agents can be part of a single dosage form, mixed together with the *Uraria*, a part thereof or an extract thereof in a single composition (simultaneous or concurrent administration).

For oral administration, a pharmaceutical composition useful in the invention can take the form of solutions, suspensions, tablets, pills, capsules, powders, granules, semisolids, sustained release formulations, elixirs, aerosols, and the like. Tablets containing various excipients such as sodium citrate, calcium carbonate and calcium phosphate are employed along with various disintegrants such as starch, preferably potato or tapioca starch, and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the *Uraria*, an extract thereof of this invention can be combined with various sweetening agents, flavoring agents, coloring agents, emulsifying agents and/or suspending agents, as well as such diluents as water, ethanol, propylene glycol, glycerin and various like combinations thereof.

The choice of formulation depends on various factors such as the mode of drug administration (e.g., for oral administration, formulations in the form of tablets, pills or capsules are preferred) and the bioavailability of the drug substance.

The term "parenteral" as used herein refers to modes of administration which include intravenous, intramuscular, intraperitoneal, intrasternal, subcutaneous, intramedullary and intraarticular injection and infusion. A pharmaceutical composition for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Aqueous solutions are especially suitable for intravenous, intramuscular, subcutaneous and intraperitoneal injection purposes. In this connection, the sterile aqueous media employed are all readily obtainable by standard techniques well-known to those skilled in the art. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The pharmaceutical compositions useful in the present invention can also contain adjuvants such as, but not limited to, preservatives, wetting agents, emulsifying agents, and dispersing agents. Prevention of the action of microorganisms can be ensured by the inclusion of various antibacterial and antifungal agents, such as for example, paraben, chlorobutanol, phenol sorbic acid, and the like. It can also be desirable to include isotonic agents such as sugars, sodium chloride, and the like. Prolonged absorption of the injectable pharmaceutical form can be brought about by the inclusion of agents that delay absorption such as aluminum monostearate and gelatin.

Administration by slow infusion is particularly useful when intrathecal or epidural routes are employed. A number of implantable or body-mountable pumps useful in delivering compound at a regulated rate are known in the art. See, e.g., U.S. Pat. No. 4,619,652.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

For purposes of transdermal (e.g., topical) administration, dilute sterile, aqueous or partially aqueous solutions (usually in about 0.1% to 5% concentration), otherwise similar to the above parenteral solutions, are prepared.

The pharmaceutical compositions useful in the invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

Compositions for rectal or vaginal administration are preferably suppositories which can be prepared by mixing the *Uraria*, a part thereof or an extract thereof of the invention with suitable non-irritating excipients or carriers such as cocoa butter, polyethylene glycol or a suppository wax which are solid at room temperature but liquid at body temperature and therefore melt in the rectum or vaginal cavity and release the drugs.

Other pharmaceutically acceptable carriers include, but are not limited to, a non-toxic solid, semisolid or liquid filler, diluent, encapsulating material or formulation auxiliary of any type, including but not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Solid pharmaceutical excipients include, but are not limited to, starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients can be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Methods of preparing various pharmaceutical compositions with a certain amount of active ingredient are known, or will be apparent in light of this disclosure, to those skilled in this art. Other suitable pharmaceutical excipients and their formulations are described in Remington's Pharmaceutical Sciences, edited by E. W. Martin, Mack Publishing Company, 19th ed. (1995.

Pharmaceutical compositions useful in the present invention can contain 1%-100% (by weight) of the *Uraria*, a part thereof or an extract thereof of this invention, preferably 10%-100%, 10%-95% or 20%-95% (by weight). In any event, the composition or formulation to be administered will contain a quantity of the *Uraria*, a part thereof or an extract thereof according to this invention in an amount effective to treat the condition, disorder or disease of the subject being treated.

One of ordinary skill in the art will appreciate that pharmaceutically effective amounts of the *Uraria*, a part thereof or an extract thereof can be determined empirically and can be employed in pure form or, where such forms exist, in pharmaceutically acceptable salt, ester or prodrug form. The agents can be administered to a patient as pharmaceutical compositions in combination with one or more pharmaceutically acceptable excipients. It will be understood that when administered to, for example, a human patient, the total daily usage of the agents or composition of the present invention will be decided within the scope of sound medical judgment by the attending physician. The specific therapeutically effective dose level for any particular patient will depend upon a variety of factors: the type and degree of the cellular response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts.

Dosaging can also be arranged in a patient specific manner to provide a predetermined concentration of the agents in the blood, as determined by techniques accepted and routine in the art.

Alternatively, the *Uraria*, a part thereof or an extract thereof can be formulated with a food grade carrier excipient, diluent and/or salt as a health food or a dietary supplement. The above-mentioned carrier excipient, diluent and/or salt can be used in the health food or a dietary supplement of the invention. Health food or dietary supplements may exist in various forms, including, but not limited to tablets, capsules, caplets, powders, drinks including shakes, solid food items including snack bars, etc.

It will be readily apparent to one of ordinary skill in the relevant arts that other suitable modifications and adaptations to the methods and applications described herein can be made without departing from the scope of the invention or any embodiment thereof. The following examples are offered to illustrate but not to limit the invention.

EXAMPLES

Materials & Methods

Plant Materials

The roots of *Uraria crinita* were collected from the Mingjian Township Farmers' Associations, Nantou, Taiwan, and were identified by Mr. Chao-Lin Kuo, School of Chinese Pharmaceutical Sciences and Chinese Medicine Resources, China Medical University, Taichung, Taiwan. A voucher specimen (M-343) was deposited in the Graduate Institute of Pharmacognosy, Taipei Medical University, Taiwan.

Reagent and Chemicals

DMSO (dimethyl sulfoxide), Thiazolyl Blue tetrazolium bromide (MTT), Triton X-100, p-nitrophenyl phosphate disodium substrate, Alizarin Red-S, cetylpyridinium chloride monohydrate, ascorbic acid, and β-glycerophosphate disodium salt hydrate were purchased from Sigma-Aldrich (Sigma, St. Louis, Mo., USA). Phosphate-buffered saline (PBS) and trypsin were purchased from Gibco (Gibco Canada Inc., Burlington, Ont., Canada). Osteoblast Optical rotations were measured on a JASCO P-1020 digital polarimeter. UV spectra were recorded on a Hitachi U-2800 UV/vis spectrometer. 1D- and 2D-nuclear magnetic resonance (NMR) spectra were measured with a Bruker AM-500 spectrometer using dimethyl sulfoxide-$d_6$, MeOH-$d_4$, and $D_2O$ solutions. HRESI-MS and ESI-MS analyses were performed with the VG Platform Electrospray ESI/MS purchased from Cell Applications (Cell Applications, Inc., San Diego, Calif., USA). All chemicals and reagents used in the study were high-grade commercial products. Other materials included BCA (bicinchoninic acid) protein assay kit (Thermo Scientific, Rockford, Ill., USA), and 4-nitrophenyl phosphate disodium salt hexahydrate (Alfa Aesar, Ward Hill, Mass., USA).

General Experimental Procedures

Optical rotations were measured on a JASCO P-1020 digital polarimeter. UV spectra were recorded on a Hitachi U-2800 UV/vis spectrometer. 1D- and 2D-nuclear magnetic resonance (NMR) spectra were measured with a Bruker AM-500 spectrometer using dimethyl sulfoxide-$d_6$, MeOH-$d_4$, and $D_2O$ solutions. HRESI-MS and ESI-MS analyses were performed with the VG Platform Electrospray ESI/MS.

Preparation of Crude Extracts and Purification

Figure 2:
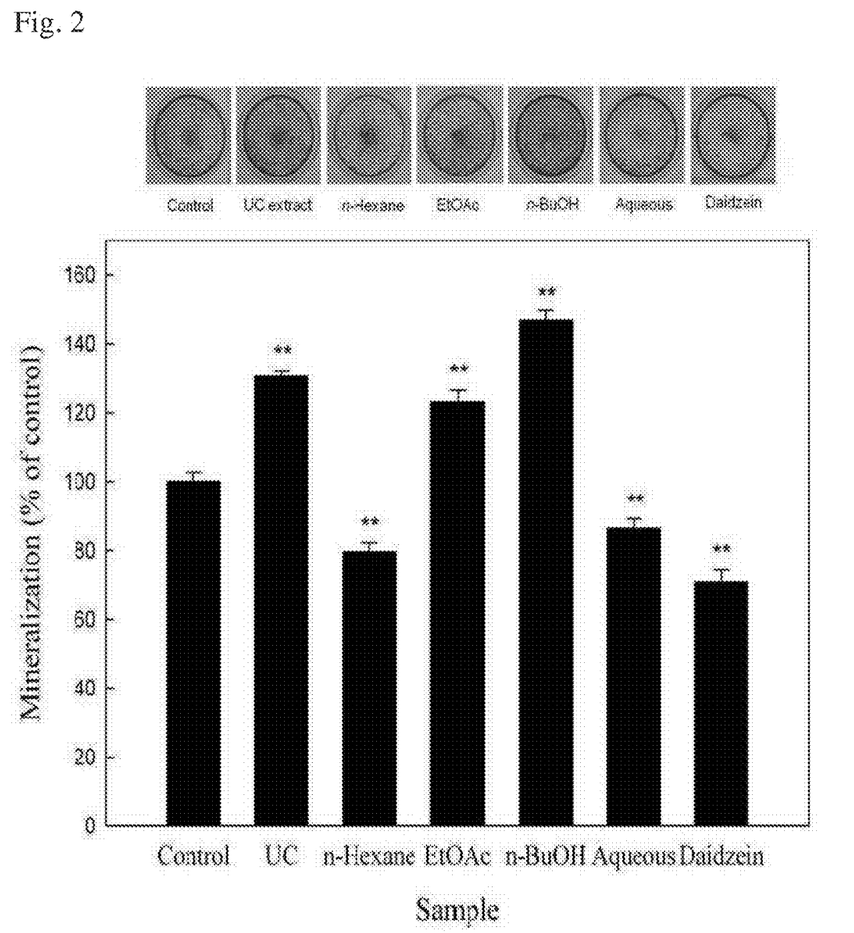
FIG. 2 shows the mineralization activities of *U. crinita* (UC) ethanolic extract and partitioned fractions in HOb cells. HOb cells were plated in 24-well plates. Three days after plating, the old medium was discarded and the cells were treated with tested extracts (100 μg/ml) in mineralizing media (Osteoblast Differentiation Medium containing ascorbic acid (50 μg/ml) and β-glycerophosphate (10 mM) for 12 days. At the end of experiment, cultures were fixed in 75% ethanol, and mineralized nodule formation was assessed by Alizarin Red-S staining. The bound staining was eluted with a solution of 10% cetylpyridinium chloride and quantified using a microtiter plate reader. Data are shown as mean±SD (n=3). *P<0.05 and **P<0.01 as compared with control (n=3).

Fresh roots (14.7 kg) of *U. crinita* were extracted three times with aqueous EtOH (95% v/v, total 120 L). After filtration, the filtrate was evaporated and dried under vacuum. The dried extract (601.4 g) was suspended in $H_2O$ and successively partitioned with n-hexane, EtOAc, and n-BuOH to yield 78.4, 32.0, and 133.9 g of extracts, respectively. The EtOAc and n-BuOH extracts had the greatest matrix mineralization activities (FIG. 2). The EtOAc extract was subjected to Sephadex LH-20 column by elution with 95% EtOH to yield nine fractions (UCE-1 to UCE-9). Fraction UCE-3 was further separated by Sephadex LH-20 column chromatography and eluted with MeOH/$H_2O$ (40-400%) to yield seventeen fractions (UCE-3-1 to UCE-3-17). Fraction UCE-3-7 was fractionated by MCI CHP-20 column chromatography with an $H_2O$-MeOH gradient elution to yield fourteen subfractions (UCE-3-7-1 to UCE-3-7-14). Compounds 2 (98.1 mg) were obtained from the UCE-3-7-4 fraction after recrystallization from MeOH/$H_2O$. Fraction UCE-4 was further separated by Sephadex LH-20 column chromatography and eluted with MeOH/$H_2O$ (50 to 100%) to yield seventeen fractions (UCE-4-1 to UCE-4-17). Fraction UCE-4-3 and UCE-4-10 were subjected to respective MCI CHP-20 columns and eluted with MeOH/$H_2O$ (30 to 100%) to yield eight (UCE-4-3-1 to UCE-4-3-8) and eleven subfractions (UCE-4-10-1 to UCE-4-10-11), respectively. Compound 11 (12.0 mg) was obtained from the UCE-4-3-2 fraction after purification by HPLC on a semi-preparative C-18 reversed-phase column with 10% MeOH as the eluting solvent system. Compound 4 (6.9 mg) was obtained from the UCE-4-10-2 fraction after purification by HPLC on a semi-preparative C-18 reversed-phase column with 25% MeCN as the eluting solvent system. Fraction UCE-5 was fractionated by MCI CHP-20 column chromatography with an $H_2O$-MeOH gradient elution to yield twenty-four subfractions (UCE-5-1 to UCE-5-24). Fractions UCE-5-15 and UCE-5-16 were subjected to Sephadex LH-20 column and eluted with MeOH/$H_2O$ (60%) to yield six (UCE-5-15-1 to UCE-5-15-6) and ten subfractions (UCE-5-16-1 to UCE-5-16-10), respectively. Compounds 3 (12.2 mg) and 1 (184.5 mg) were obtained from the UCE-5-15-1 and UCE-5-16-9 fractions after purification by HPLC on a semi-preparative C-18 reversed-phase column with 55% MeOH as the eluting solvent system. The n-BuOH extract was subjected to Diaion HP-20 column by elution with an $H_2O$-MeOH gradient elution to yield six subfractions (UCB-1 to UCB-6). Fractions UCB-3, UCB-4, and UCB-5 were further separated by respective Sephadex LH-20 columns and eluted with 95% EtOH to yield six (UCB-3-1 to UCB-3-6), nine (UCB-4-1 to UCB-4-9), and six fractions (UCB-5-1 to UCB-5-6), respectively. Fractions UCB-3-3 and UCB-5-2 were separated by MCI CHP-20 column chromatography with an $H_2O$-MeOH gradient elution to yield six (UCB-3-3-1 to UCB-3-3-6) and eight subfractions (UCB-5-2-1 to UC-B-5-2-8). Compounds 7 (38.3 mg) and 8 (15.3 mg) were obtained from the UCB-3-3-2 fraction. Compounds 5 (58.6 mg) and 6 (7.6 mg) were obtained from the UCB-3-3-3 and UCB-5-2-1 fractions after purification by respective HPLC on a semi-preparative C-18 reversed-phase column with 20% MeOH as the eluting solvent system. Fractions UCB-4-3 and UCB-4-4 were separated by MCI CHP-20 column and eluted with MeOH/$H_2O$ (60 to 100% and 20 to 100%, respectively) to yield four (UCB-4-3-1 to UCB-4-3-4) and nine subfractions (UCB-4-4-1 to UCB-4-4-9). Compound 9 (38.5 mg) was obtained from the UCB-4-3-3 fraction after purification by HPLC on a semi-preparative C-18 reversed-phase column with 20% MeOH as the eluting solvent system. Compound 10 (13.5 mg) was obtained from the UCB-4-4-3 fraction after purification by HPLC on a semi-preparative C-18 reversed-phase column with 40% MeOH as the eluting solvent system.

Acid Hydrolysis of 3

One milligram of 3 was hydrolyzed with 6 N HCl at 80° C. in a heating block for 6-8 hours. The mixture was cooled and evaporated to remove the acid, then resuspended in milli-Q water and passed through a Millipore-GX nylon membrane before analysis [18]. Monosaccharides of 3 and polysaccharide hydrolysates were separated on a high-performance anion-exchange chromatographic (HPAEC) system (Dionex, Sunnyvale, Calif.) and an anion-exchange column (Carbopac PA-10, 4.6×250 mm) The analysis of the monosaccharides was carried out using an isocratic 18 mM NaOH solution at ambient temperature.

Apigenin 6-C-(β-D-apiofuranosyl(1→2)-α-D-xylopyranoside (3): yellow solid; $[\alpha]^{22}_D$+21 (c 0.5, MeOH); UV (MeOH) $\lambda_{max}$ (log ε): 272 (4.36), 329 (4.35) nm; $^1$H-NMR (DMSO-$d_6$, 500 MHz) and $^{13}$C-NMR (DMSO-$d_6$, 125 MHz), see Table 1; HRESI-MS m/z 535.1459 [M+H]$^+$ (calcd for $C_{25}H_{27}O_{13}$, 535.1452).

Cell Culture

Human osteoblasts (HOb) were primary cells derived from a 63-year-old caucasian female from a normal femoral bone and obtained from Cell Applications (San Diego, Calif., USA). HOb cells were grown in Osteoblast Growth Medium and maintained at 37° C. in 5% $CO_2$ humidified atmosphere. The medium was changed every other day. To maintain exponential growth, the cells were subcultured every 7 days. HOb cells were used for cell viability, differentiation, and mineralization assays.

Cell Viability Assay

The cell viability of *U. crinita* extract and its constituents were determined using the MTT assay as described elsewhere (Scudiero et al., 1988). HOb cells were seeded in 96-well plates at a density of $4 \times 10^3$ cells per well. Twenty-four hours after plating, the old medium was discarded and the cells were treated with tested extracts or compounds. After 72 hours incubation, the medium was discarded and MTT reagent was added to each well and incubated for 4 hours. Then the medium was discarded, and 100 µl of DMSO was added to all wells and mixed thoroughly to dissolve the dark blue crystals. The absorbance at 600 nm was recorded using an ELISA reader. The cell viability of *U. crinita* extract and its constituents were determined using the MTT assay as described elsewhere (Scudiero et al., 1988). HOb cells were seeded in 96-well plates at a density of $4 \times 10^3$ cells per well. Twenty-four hours after plating, the old medium was discarded and the cells were treated with tested extracts or compounds. After 72 hours incubation, the medium was discarded and MTT reagent was added to each well and incubated for 4 hours. Then the medium was discarded, and 100 µl of DMSO was added to all wells and mixed thoroughly to dissolve the dark blue crystals. The absorbance at 600 nm was recorded using an ELISA reader. The cell viability of *U. crinita* extract and its constituents were determined using the MTT assay as described elsewhere (Scudiero et al., 1988). HOb cells were seeded in 96-well plates at a density of $4 \times 10^3$ cells per well. Twenty-four hours after plating, the old medium was discarded and the cells were treated with tested extracts or compounds. After 72 hours incubation, the medium was discarded and MTT reagent was added to each well and incubated for 4 hours. Then the medium was discarded, and 100 µl of DMSO was added to all wells and mixed thoroughly to dissolve the dark blue crystals. The absorbance at 600 nm was recorded using an ELISA reader.

Alkaline Phosphatase (ALP) Assay

The alkaline phosphatase (ALP) activities of *U. crinita* extract and its constituents were measured with p-nitrophenyl phosphate as the substrate. HOb cells were seeded in 96-well plates at a density of $4 \times 10^3$ cells per well. Twenty-four hours after plating, the old medium was discarded and the cells were treated with tested extracts or compounds in Osteoblast Differentiation Medium. After 72 hours incubation, the medium was discarded and the cells rinsed twice with cold PBS, and cells were lysed with lysis buffer (PBS containing 0.1% Triton X-100). The cellular protein concentration in supernatant was determined after incubation with BCA (bicinchoninic acid) protein reagent for 1 hour at 37° C. The reaction was stopped by adding 1M NaOH, and absorbance measured at 560 nm. Furthermore, the ALP activity in supernatant was assayed by incubation for 1 hour at 37° C. in 0.1 M $NaHCO_3$—$Na_2CO_3$ buffer, pH 10, containing 0.1% Triton X-100, 2 mM $MgSO_4$, and 6 mM p-nitrophenyl phosphate. The reaction was stopped by adding 1M NaOH and absorbance was measured at 405 nm. Each value was normalized to the protein concentration.

Mineralized Matrix Formation Assay

The mineralization activities of *U. crinita* extract and its constituents were measured by Alizarin Red-S staining of calcium. HOb cells were seeded in 24-well plates at a density of $7 \times 10^4$ cells per well. Three days after plating, the old medium was discarded and the cells were treated with tested extracts or compounds in mineralizing media (Osteoblast Differentiation Medium) containing ascorbic acid (50 µg/ml) and β-glycerophosphate (10 mM) for 12 days. At the end of experiment, cultures were fixed in 75% ethanol, and calcium deposits were stained for 15 minutes at room temperature with Alizarin Red-S solution (40 mM, pH 4.2). The bound staining was eluted with a solution of 10% (w/v) cetylpyridinium chloride in 10 mM sodium phosphate (pH 7.0) and quantified using a ELISA reader at 550 nm.

Statistical Analysis

Student's t test was used for determining the statistically significant differences between the values of various experimental groups. Data were expressed as means±SD and a P-value<0.05 was considered statistically significant.

Example 1

Figure 1:
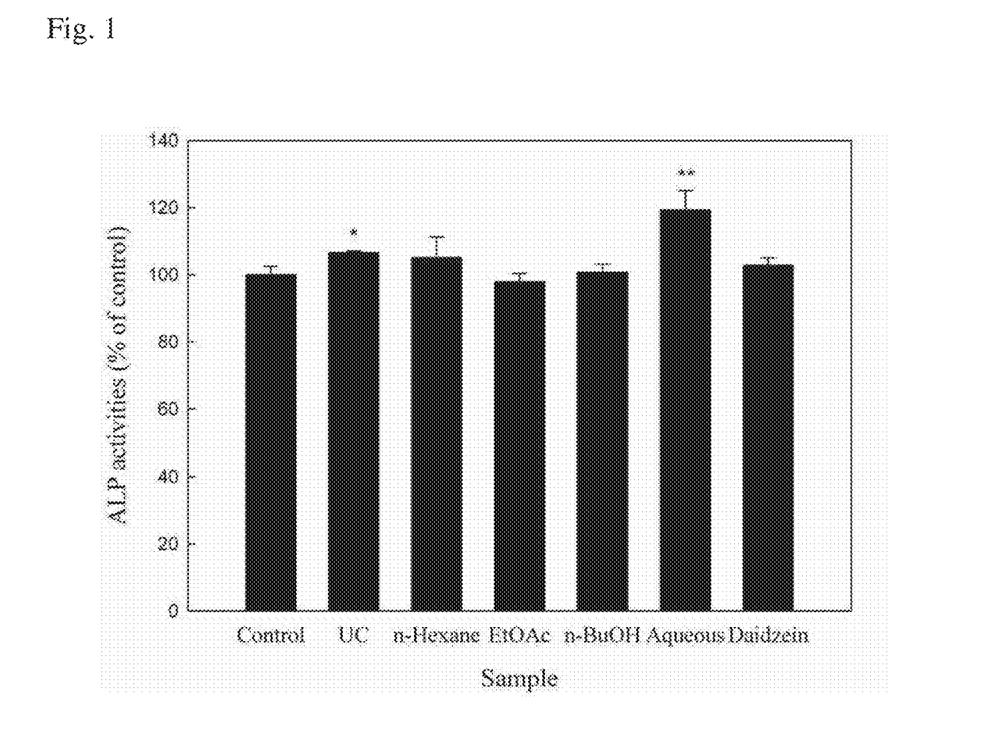
FIG. 1 shows the ALP activities of *U. crinita* (UC) ethanolic extract and partitioned fractions in HOb cells. HOb cells were seeded in 96-well plates. Twenty-four hours after plating, the old medium was discarded and the cells were treated with tested extracts (100 μg/ml) in Osteoblast Differentiation Medium for 72 h. ALP activity was assessed using the p-nitrophenyl phosphate disodium substrate. Data are shown as mean±SD (n=3). *P<0.05 and **P<0.01 as compared with control (n=3).

Promoting Osteogenic Differentiation and Matrix Mineralization of *U. crinita* Extracts in HOb Cells The 95% ethanol (EtOH) extract of the roots of *U. crinita* (UC) was submitted to extractive and chromatographic analyses using a bio-guided method. The 95% EtOH crude extract was suspended in $H_2O$ and sequentially partitioned with n-hexane, EtOAc, and n-BuOH to yield four fractions. The cell proliferation of crudes in HOb cells was evaluated by MTT assay. Our results showed that none of the crudes were found to cause significant cytotoxicity or proliferation to the HOb cells at concentration of 100 µg/mL or below (data not shown). ALP activity is a major osteoblast differentiation marker. We examined the effect of extracts on osteoblastic differentiation by determining ALP activity in HOb cells. The results showed that 95% EtOH crude extract and aqueous fraction showed increased ALP activities by 106.51±0.44, and 119.36±5.64% at 100 µg/mL (FIG. 1) in HOb cells after 72 hours of treatment, respectively. Furthermore, we tested the effect of crudes on osteoblastic mineralization by determining bone nodule formation in HOb cells. Hitochemical alizarin red staining of mineralized nodules was carried out on day 12. The results showed that 95% EtOH crude extract, EtOAc, and n-BuOH fractions showed increasing mineralization activities by 130.45±1.51, 123.11±3.28, and 146.73±2.85% at 100 µg/mL (FIG. 2), respectively.

Example 2

Bio-Guided Isolation and Identification of Active Compounds from *U. crinita*

Figure 3:
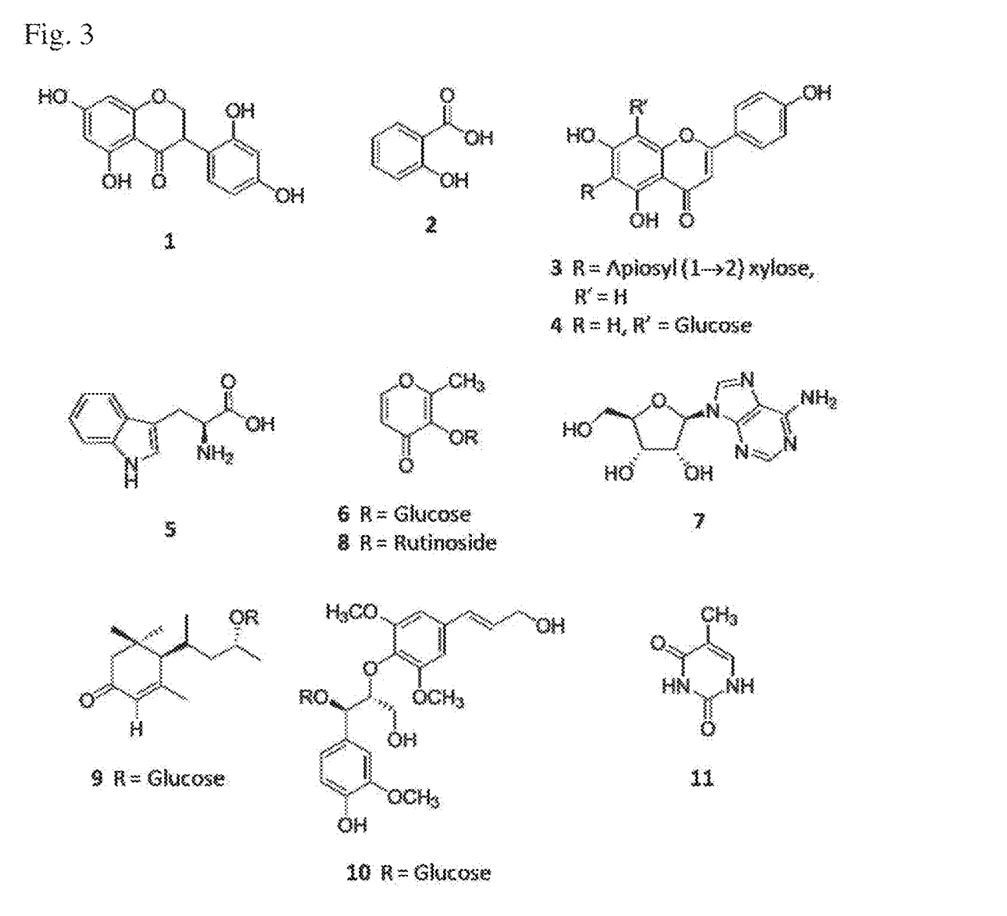
FIG. 3 shows schematic representation of the chemical structures of the isolated constituents from *U. crinita*.

The active EtOAc and n-BuOH fractions were submitted to various column chromatography and HPLC purification and yielded new compound (3), along with ten known compounds, dalbergioidin (1) (Durango, Quinones, Torres, Rosero, Gil & Echeverri, 2002), salicylic acid (2) (Scott, 1972), vitexin (4) (Krafczyk & Glomb, 2008), tryptophan (5) (Lee & Phillips, 1992), maltol-3-O-β-D-glucopyranoside (6) (Ono, Masuoka, Tanaka, Ito & Nohara, 2001), adenosine (7) (Moyroud & Strazewski, 1999), spatholosineside A (8) (Yin, Liu, Wang, Tu, Liang & Zhao, 2008), byzantionoside B (9) (Matsunami, Otsuka & Takeda, 2010), (7R,8R)-threo-guaiacylglycerol-8-O-4'-sinapyl ether 7-O-β-D-glucopyranoside (10)

(Machida, Sakamoto & Kikuchi, 2009), and thymine (11) (Pouchert, 1993) (FIG. 3). These known compounds were identified by comparison of their spectral data (UV, $^1$H-NMR, $^{13}$C-NMR, ESI-MS) with corresponding data in the literature or with authentic samples.

Figure 4:
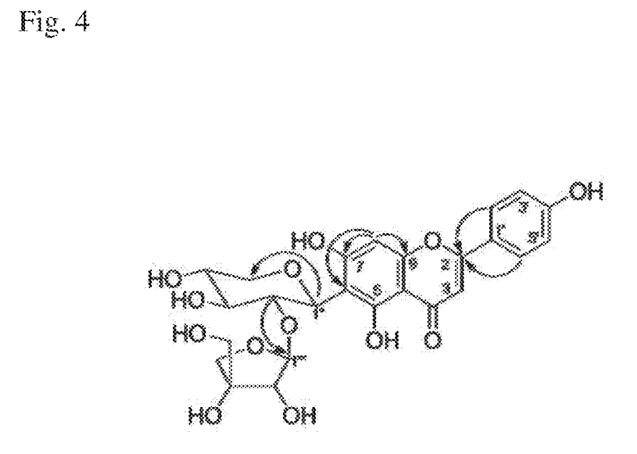
FIG. 4 shows HMBC correlations (H→C) of apigenin 6-C-(β-D-apiofuranosyl(1→2)-α-D-xylopyranoside (3).

The new compound 3 was obtained as a yellow power. The molecular formula of 3 was determined to be $C_{25}H_{26}O_{13}$ from its positive HRESI-MS m/z: 535.1459 [M+H]$^+$ (calc. for $C_{25}H_{27}O_{13}^+$, 535.1452), which was consistent with its nuclear magnetic resonance (NMR) data (Table 1). The UV spectrum showed absorption bands at $\lambda_{max}$ 272 and 329 nm, and the NMR spectrum showed $\delta_H$ 6.75 (1H, s, H-3) together with the signals of $\delta_C$ 102.8 (C-3), 163.5 (C-2), and 181.8 (C-4), which suggested the presence of flavone moieties. The presence of signals at $\delta_H$ 6.91 (2H, d, J=8.8 Hz, H-3', H-5'), and 7.92 (2H, d, J=8.8 Hz, H-2', H-6') in an $A_2X_2$ coupling system, together with the signals of $\delta_C$ 116.0 (C-3', C-5'''), and 128.5 (C-2', C-6''') observed in the NMR spectra suggested monosubstituted aromatic moiety (ring B) in 3. In the Heteronuclear Multiple Bond Correlation (HMBC) spectrum (FIG. 4), one aromatic signal, $\delta_H$ 6.51 (1H, s, H-8), was assigned at H-8, due to the long-range coupling with C-6, C-7, and C-9, respectively. These data suggested that 3 has a 5,7,4'-trihydroxyflavone (apigenin) skeleton. The NMR spectrum also showed two sugar signals $\delta_H$ 2.52 to 5.25 and $\delta_C$ 64.5 to 109.1. After the acid hydrolysis of 3, the aqueous layer was separated by HPLC and compared with standards to yield only one glycoside: apiose. The presence of other sugar (xylose) was determined by NMR, HSQC, COSY and HMBC spectrum. The above evidence indicated that 3 was an apigenin substituted with xylose and apiose moieties. The 6-C-glycosylation of apigenin with xylose was confirmed at lower field than that ($\delta_C$ 100.1) of luteolin about 8 ppm, and C-1'' signal appeared near at $\delta_C$ 72.1 in NMR analysis and acid hydrolysis (Dubois, Zoll, Bouillant & Chopin, 1982). The α-configuration of D-xyloside and the β-configuration of D-apioside could be deduced by the coupling constants of the anomeric protons H-1'' and H-1''' (Shie et al., 2010). The position of the β-D-apiofuranoside and α-D-xylopyranoside linkage (C-1'''C-2'') was confirmed at C-1'' at $\delta_C$ 198.1 and H-2'' at $\delta_H$ 4.27 (1H, brs) by HMBC correlations. Based on the aforementioned data, the structure of 3 was determined as apigenin 6-C-(β-D-apiofuranosyl(1→2)-α-D-xylopyranoside.

TABLE 1

$^1$H and $^{13}$C NMR data (DMSO-d$_6$, 500 and 125 Hz) for compound 3.

| Position | $\delta_H$ | $\delta_C$ |
|---|---|---|
| 2 | | 163.5 |
| 3 | 6.75 (s) | 102.8 |
| 4 | | 181.8 |
| 5 | | 161.2 |
| 6 | | 108.8 |
| 7 | | 163.5 |
| 8 | 6.51 (s) | 94.0 |
| 9 | | 156.4 |
| 10 | | 103.2 |
| 1' | | 121.1 |
| 2', 6' | 7.92 (d, J = 8.8) | 128.5 |
| 3', 5' | 6.91 (d, J = 8.8) | 116.0 |
| 4' | | 161.2 |
| 1'' | 4.55 (brs) | 72.1 |
| 2'' | 4.27 (brs) | 72.6 |
| 3'' | 3.54 (m) | 75.1 |
| 4'' | 3.74 (m) | 69.4 |
| 5'' | 3.51 (m) 3.77 (m) | 70.1 |

TABLE 1-continued $^1$H and $^{13}$C NMR data (DMSO-d$_6$, 500 and 125 Hz) for compound 3.

| Position | $\delta_H$ | $\delta_C$ |
|---|---|---|
| 1''' | 5.15 (brs) | 109.1 |
| 2''' | 3.58 (m) | 75.9 |
| 3''' | | 79.0 |
| 4''' | 2.52 (m) 3.08 (d, 7 = 9.3) | 73.6 |
| 5''' | 2.99 (d, J = 11.0) 3.18 (d, J = 11.0) | 64.5 |
| 5-OH | 13.50 (brs) | |

Example 3

Cell Viability of Compounds Isolated from *U. crinita* on HOb Cells

Figure 5:
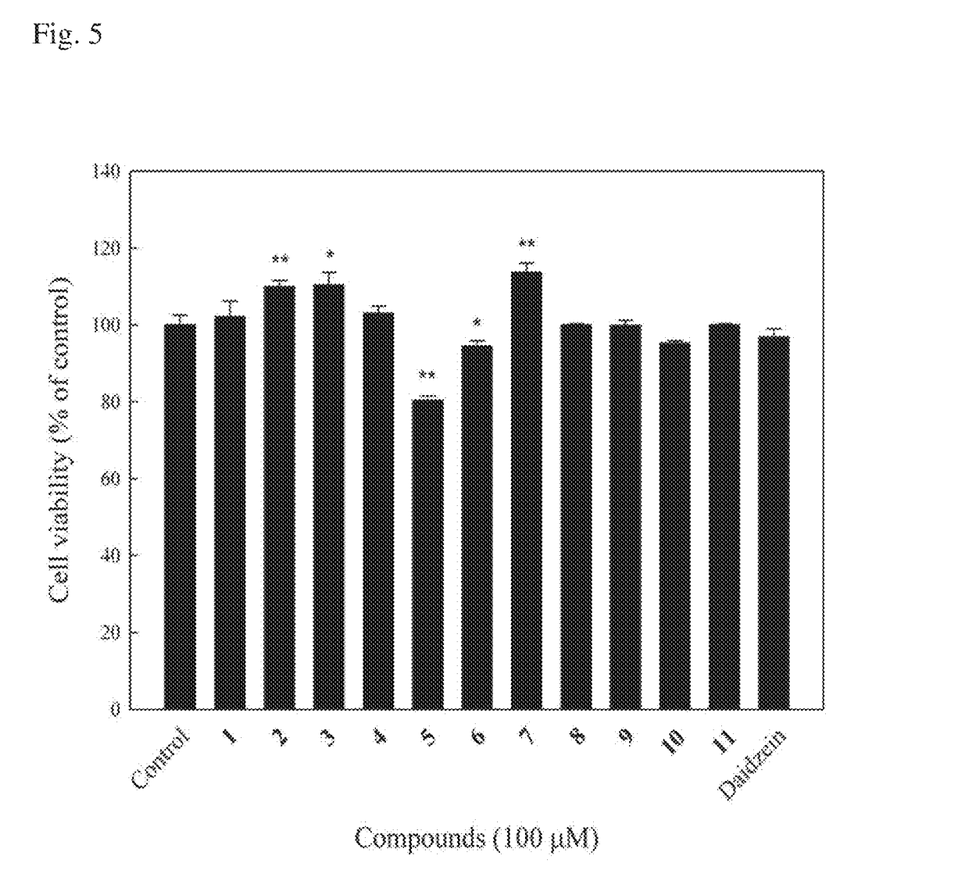
FIG. 5 shows the cell viabilities of isolated compounds from *U. crinita* (UC) in HOb cells. HOb cells were seeded in 96-well plates. Twenty-four hours after plating, the old medium was discarded and the cells were treated with tested compounds (100 μM) in Osteoblast Differentiation Medium for 72 h. Cell viability was assessed using the MTT assay. Data are shown as mean±SD (n=3). *P<0.05 and **P<0.01 as compared with control (n=3).

HOb cells were incubated with compounds isolated from *U. crinita* for 72 hours and cell viability was measured by MTT assay. Our results exhibited that only compound (5) showed slight inhibition of cell viability with a value of 80.43±1.11% at 100 μM. The results are shown in FIG. 5.

Example 4

ALP Activity of Compounds Isolated from *U. crinita* on HOb Cells

Figure 6:
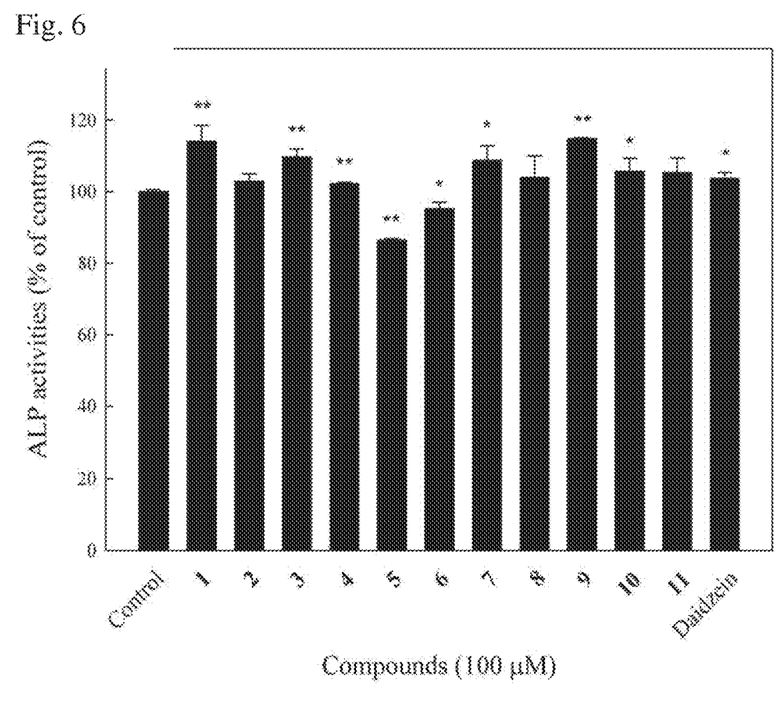
FIG. 6 shows the ALP activities of isolated compounds from *U. crinita* (UC) in HOb cells. HOb cells were seeded in 96-well plates. Twenty-four hours after plating, the old medium was discarded and the cells were treated with tested compounds (100 μM) in Osteoblast Differentiation Medium for 72 h. ALP activity was assessed using the p-nitrophenyl phosphate disodium substrate. Data are shown as mean±SD (n=3). *P<0.05 and **P<0.01 as compared with control (n=3).

In order to investigate the effect of compounds isolated from *U. crinita* on the osteoblastic differentiation, alkaline phosphate (ALP) activity, which is a kind of biomarker in bone early differentiation, was measured in HOb cells. The plant constituent, daidzein, was used as the positive control (Jia, Wang, Xie, Wang & Zhang, 2003). Among these compounds, four compounds, dalbergioidin (1), apigenin 6-C-(β-D-apiofuranosyl(1→2)-α-D-xylopyranoside (3), adenosine (7), and byzantionoside B (9), were found to have significantly increased the ALP activities in HOb cells by 114.10±4.41, 109.68±2.20, 108.70±4.14, and 114.81±0.18% at 100 μM, respectively (FIG. 6).

Example 5

Mineralization of Compounds Isolated from *U. crinita* on HOb Cells

Figure 7:
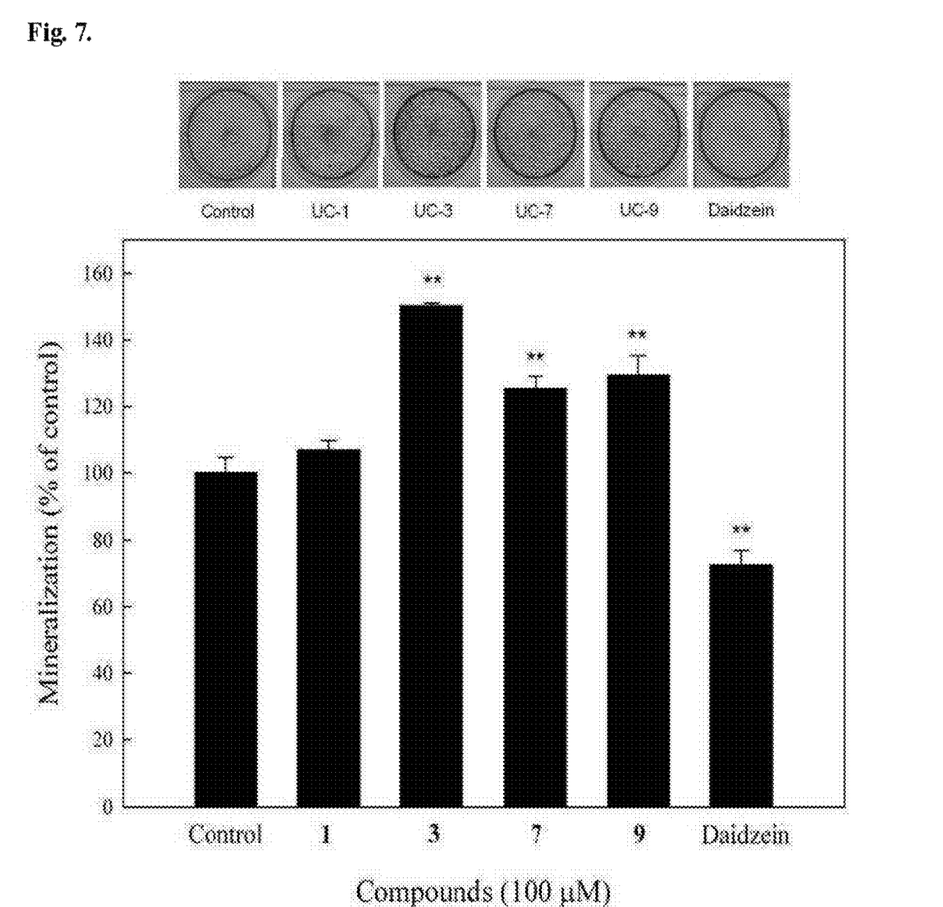
FIG. 7 shows the mineralization activities of isolated compounds from *U. crinita* (UC) in HOb cells. HOb cells were plated in 24-well plates. Three days after plating, the old medium was discarded and the cells were treated with tested compounds (100 μM) in mineralizing media (Osteoblast Differentiation Medium) containing ascorbic acid (50 μg/ml) and β-glycerophosphate (10 mM) for 12 days. At the end of experiment, cultures were fixed in 75% ethanol, and mineralized nodule formation was assessed by Alizarin Red-S staining. The bound staining was eluted with a solution of 10% cetylpyridinium chloride and quantified using a microtiter plate reader. Data are shown as mean±SD (n=3). *P<0.05 and **P<0.01 as compared with control (n=3).

Alizarin red staining which is widely used to detect the presence of calcium in cells (Wang, Liu, Maye & Rowe, 2006) was carried out to investigate the effect of compounds isolated from *U. crinita* on bone mineralization in HOb cells cultured for 12 days in the presence of test compounds, ascorbic acid and β-glycerophosphate. The results showed that new compound 3, dalbergioidin (1), adenosine (7), and byzantionoside B (9), significantly increased the formation of mineralized bone nodules in HOb cells by 150.10±0.80, 107.09±2.80, 125.21±3.75, and 129.21±6.13% at 100 μM, respectively (FIG. 7). These results revealed that new compound 3 exhibited the most potent mineralization activity of human osteoblast cells. Alizarin red staining, which is widely used to detect the presence of calcium in cells (Wang, Liu, Maye & Rowe, 2006). was carried out to investigate the effect of compounds isolated from *U. crinita* on bone mineralization in HOb cells cultured for 12 days in the presence of test compounds, ascorbic acid and β-glycerophosphate. The results showed that new compound 3, dalbergioidin (1), adenosine (7), and byzantionoside B (9), significantly increased the formation of mineralized bone nodules in HOb cells by 150.10±0.80, 107.09±2.80, 125.21±3.75, and 129.21±6.13% at 100 μM, respectively (FIG. 7). These results revealed that new compound 3 exhibited the most potent mineralization activity of human osteoblast cells.

Example 6

Neuroprotection Effect of *U. crinita* Extracts

The NGF (nerve growth factor)-Induced PC12 Cell Differentiation assay was used as nerve injury testing model and 6-hydroxydopamine was used to induce the nerve injury. The extracts of *U. crinite* roots prepared as stated above were used in the assay. It was found that the ethyl acetate extract and butanol extract have advantageous neuroprotection effect. The cell survival rates of PC12 cells damaged by 6-hydroxydopamine increase from 50.22+/−0.55% to 62.88+/−1.10% (the cells treated with ethyl acetate extract) and 61.54+/−1.48% (the cells treated with butanol extract).

What is claimed is:

1. A method for treating a bone disease in a subject in need of such treatment, the method comprises administering to the subject a composition comprising 20% to 95% of *Uraria* extract, wherein the *Uraria* extract is an ethyl acetate extract or butanol extract obtained from the *Uraria*, wherein the *Uraia* is *Uraria* root, and wherein the bone disease is osteoporosis.

2. The method of claim 1, wherein the *Uraria* is selected from the group consisting of: *Uraria crinita* (L.) Desv. ex DC., *Uraria lagopodioides* (L.) Desv. ex DC., *Uraria picta* (Jacq.) Desv. ex DC., *Uraria neglecta* Prain, *Uraria acaulis* Schindl, *Uraria acuminata* Kurz, *Uraria balansae* Schindl., *Uraria barbata* Lace, *Uraria campanulata* (Benth.) Gagnep., *Uraria candida* Backer, *Uraria clarkei* Gagnep., *Uraria cochinchinensis* Schindl., *Uraria cordifolia* Wall., *Uraria crinita* (L.) DC., *Uraria cylindracea* Benth., *Uraria fujianensis* Y. C. Yang & P. H. Huang, *Uraria gossweileri* Baker f., *Uraria kurzii* Schindl., *Uraria lacei* Craib, *Uraria lagopodoides* (L.) DC., *Uraria lagopus* DC., *Uraria longibracteata* Y. C. Yang & P. H. Huang, *Uraria pierrei* Schindl., *Uraria poilanei* Phon, *Uraria prunellifolia* Baker, *Uraria rotundata* Craib, *Uraria rufescens* (DC.) Schindl. and *Uraria sinensis* (Hemsl.) Franch.

3. The method of claim 2, wherein the *Uraria* is *Uraria crinita* (L.) Desv. ex DC., *Uraria lagopodioides* (L.) Desv. ex DC., *Uraria picta* (Jacq.) Desv. ex DC. or *Uraria neglecta* Prain.

4. The method of claim 1, wherein the *Uraria* extract is produced by the following steps: extracting *Uraria* with ethanol to obtain an ethanol extract and extracting the ethanol extract with ethyl acetate or butanol to obtain an ethyl acetate extract or butanol extract.

5. The method of claim 2, wherein the *Uraria* extract is ethyl acetate extract or butanol extract obtained from the ethanol extract of *Uraria* root.

6. The method of claim 1, wherein the ethyl acetate extract contains Apigenin 6-C-($\beta$-D-apiofuranosyl(1→2)-$\alpha$-D-xylopyranoside.

7. A method for treating neuronal injury in a subject in need of such treatment, which comprises administering to the subject a composition comprising 20% to 95% of *Uraria* extract, wherein the *Uraria* extract is an ethyl acetate extract or butanol extract obtained from the *Uraria*, and wherein the *Uraria* is a *Uraria* root.

8. The method of claim 7, wherein the *Uraria* extract is produced by the following steps: extracting *Uraria* with ethanol to obtain an ethanol extract and extracting the ethanol extract with ethyl acetate or butanol to obtain an ethyl acetate extract or butanol extract.

9. The method of claim 7, wherein the *Uraria* extract is ethyl acetate extract or butanol extract obtained from an ethanol extract of the *Uraria* root.

10. The method of claim 7, wherein the ethyl acetate extract contains Apigenin 6-C-($\beta$-D-apiofuranosyl(1→2)-$\alpha$-D-xylopyranoside.

* * * * *